United States Patent
Tanger et al.

(12)

(10) Patent No.: US 6,444,861 B1
(45) Date of Patent: Sep. 3, 2002

(54) PROCESS FOR THE CLEAVAGE OF ALKYLARYL HYDROPEROXIDES

(75) Inventors: Uwe Tanger, Bochum; Manfred Weber, Haltern, both of (DE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/978,718

(22) Filed: Oct. 18, 2001

(30) Foreign Application Priority Data

Oct. 18, 2000 (DE) ......................................... 100 51 581

(51) Int. Cl.[7] ............................................... C07C 37/08
(52) U.S. Cl. ...................................................... 568/798
(58) Field of Search ......................................... 568/798

(56) References Cited

U.S. PATENT DOCUMENTS 5,254,751 A  * 10/1993  Zakoshansky
5,530,166 A  *  6/1996  Zakoshansky
6,057,483 A  *  5/2000  Zakoshansky
6,307,112 B1 * 10/2001  Weber

* cited by examiner

*Primary Examiner*—Michael L. Shippen
(74) *Attorney, Agent, or Firm*—Oblon, Spivak, McClelland, Maier & Neustadt, P.C.

(57) ABSTRACT

A process for the cleavage of alkylaryl hydroperoxides includes steps for producing a mixture of a concentrate that contains at least one alkylaryl hydroperoxide to be cleaved and a cleavage product obtained from the cleavage of an alkylaryl hydroperoxide, dividing this mixture into at least two parts and cleaving the alkylaryl hydroperoxides in parallel at different temperatures. One of the two parts is treated at a temperature sufficiently high for an integrated thermal post-treatment to be achieved. The process consumes less energy since less steam has to be used. Problems which can result from fouling in heat exchangers are largely prevented. No second feed point for alkylaryl hydroperoxide has to be provided. The process can be used in the preparation of phenol and acetone by the Hock method.

33 Claims, 2 Drawing Sheets

PROCESS FOR THE CLEAVAGE OF ALKYLARYL HYDROPEROXIDES

BACKGROUND OF THE INVENTION

1. Field of the Invention

The invention relates to an improved process and apparatus for the cleavage of alkylaryl hydroperoxides. The invention is particularly useful for the acid-catalyzed cleavage of cumene hydroperoxide (CHP) to give phenol and acetone.

2. Discussion of the Background

The process of acid-catalyzed cleavage of cumene hydroperoxide to phenol and acetone has been of particular industrial importance for a long time and continues to be so today. In the preparation of phenol from cumene by the Hock process, cumene is oxidized in a first reaction step, known as oxidation, to form cumene hydroperoxide (CHP) and the CHP is subsequently concentrated to from 65 to 90% by weight in a vacuum distillation step known as concentration. In a second reaction step, known as cleavage, the CHP is cleaved into phenol and acetone by action of an acid, usually sulfuric acid. In this step, dimethyl phenyl carbinol (DMPC), formed as a side product of the oxidation, is cleaved into α-methylstyrene (AMS) and water in an equilibrium reaction. DMPC also reacts with CHP to form dicumyl peroxide (DCP). Unreacted DMCP remains in the cleavage product. After neutralization of the cleavage product, the mixture is usually worked up by distillation.

In the cleavage reaction, high boilers (dimers, cumylphenols, bisphenols) are formed from AMS and DMPC and are later separated as residue in the distillation. The AMS present after the neutralization is hydrogenated to cumene during distillation and returned for oxidation. Unreacted DMPC remaining after cleavage ends up as either a high boiler in the residue, or reacts further in the hot phenol columns to form AMS from which high-boiling secondary components are in turn formed. DCP is stable at customary cleavage temperatures (from 50 to 70° C.). It can decompose thermally in the hot phenol columns to form o-cresols. On the other hand, DCP can be cleaved at temperatures above 80° C. in the presence of acid into phenol, acetone and AMS. It is therefore advantageous to achieve complete reaction of the remaining DMPC and the DCP by selectively increasing the temperature in the presence of the acid catalyst in the cleavage. This converts most of the DMPC into AMS and converts DCP virtually completely into phenol, acetone and AMS.

3. Description of the Related Art

Thermal post-treatment of the cleavage product has been described in U.S. Pat. No. 2,757,209, in which temperatures above 100° C., especially in the range from 110 to 120° C., were used. The objective of this thermal post-treatment was complete dehydration of the DMPC to AMS. U.S. Pat. No. 4,358,618, on the other hand, describes a thermal post-treatment with the objective of completely converting the DCP formed in the cleavage into phenol, acetone and AMS, by employing temperatures of from 120 to 150° C. U.S. Pat. No. 5,254,751 describes thermal post-treatment with the same objective as that of U.S. Pat. No. 4,358,618, but with temperatures in the range from 80 to 110° C. Finally, post-treatment is carried out above 150° C. in DE 197 55 026 A1. Thus drastically different optimum temperature ranges for the thermal post-treatment of the cleavage product from the production of phenol have been described.

In all the above-mentioned thermal post-treatment processes, the cleavage product is first heated by means of steam in heat exchangers and, after a sufficient reaction time, is then cooled by means of water in heat exchangers. Depending on the temperature chosen for the thermal post-treatment, this results in specific steam consumption of about 0.2 metric tons of steam per metric ton of phenol. It has been found that temperatures above 100° C., especially temperatures above 120° C., result in increased deposition (fouling) of high-boiling by-products in the heat exchangers. This deposition is associated with a drastic impairment of heat transfer. Especially in the apparatuses for heating the product by means of steam, organic deposits formed on the hot heat exchange surfaces on the product side require these apparatuses to be cleaned at relatively short intervals, such as a few weeks. As the temperature increases, the degree of fouling also increases.

Heating the cleavage product by means of a recuperator in which the cleavage product entering the thermal post-treatment is preheated by the cleavage product leaving the thermal post-treatment enables the steam consumption to be reduced. The problem of fouling is not prevented by this method, as is described in U.S. Pat. No. 6,057,483.

DE 100 21 482 proposed a solution to this problem. In this process for the thermal post-treatment of the cleavage product resulting from the acid-catalyzed cleavage of cumene hydroperoxide into phenol and acetone, the cleavage product to be thermally treated is heated in a reactor using the heat of reaction of at least one exothermic reaction occurring in this reactor. This achieves high selectivity in the post-treatment while at the same time lowering energy costs and achieving a higher operating period of the heat exchangers by avoidance of fouling.

A disadvantage of this process, in which the heat of reaction liberated in the cleavage of CHP is normally used, is the fact that in order to obtain high residual CHP contents at the outlet of the cleavage product and thus in the circulated stream, it is necessary to employ high circulating flows so as to be able to dilute the concentrate entering the cleavage to a sufficient extent. Although a second introduction of CHP concentrate is more advantageous from this point of view, as known to those skilled in the art, it requires additional safety equipment and is therefore very costly.

BRIEF DESCRIPTION OF THE FIGURES

An apparatus and a process according to the prior art are shown in FIG. 1. Different embodiments of the process and apparatus according to the invention are depicted in FIGS. 2 to 5. The Figures do not limit the invention to any single embodiment.

SUMMARY OF THE INVENTION

Objects of the Present Invention

Figure 1:
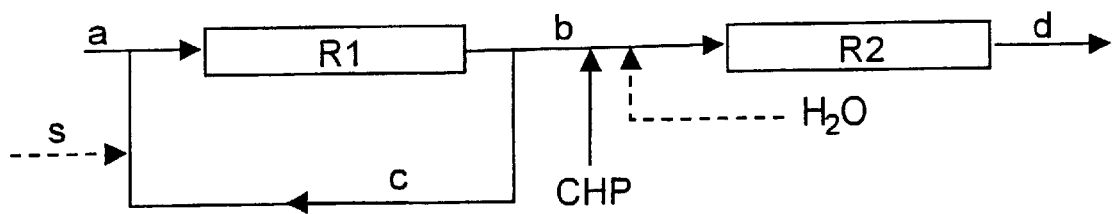

It is an object of the invention to provide a simple process for the cleavage of cumene hydroperoxide in which the thermal post-treatment of the cleavage product resulting from the acid-catalyzed cleavage of cumene hydroperoxide into phenol and acetone can be eliminated in order to achieve high safety, low capital costs and a high reliability by avoidance of fouling.

Surprisingly, it has been found that in a process for the cleavage of alkylaryl hydroperoxides in which a mixture of a concentrate comprising at least one alkylaryl hydroperoxide to be cleaved and a cleavage product obtained from the cleavage of an alkylaryl hydroperoxide, is divided into at least two parts and the alkylaryl hydroperoxides in these parts are cleaved in parallel at different temperatures, the process achieves both high selectivity in the cleavage while simultaneously lowering energy costs, giving a higher operating period of the heat exchangers by avoidance of fouling, and providing a higher margin of safety than is the case in conventional processes.

Accordingly the present invention provides a process for the acid-catalyzed cleavage of alkylaryl hydroperoxides, which comprises producing a mixture of a concentrate comprising at least one alkylaryl hydroperoxide to be cleaved and a cleavage product obtained from the cleavage of an alkylaryl hydroperoxide, dividing this mixture into at least two parts and cleaving the alkylaryl hydroperoxides in these parts in parallel at different temperatures.

The present invention likewise provides a process for preparing phenol by cleavage of cumene hydroperoxide, which comprises producing a mixture of a concentrate comprising at least one alkylaryl hydroperoxide to be cleaved and a cleavage product obtained from the cleavage of an alkylaryl hydroperoxide, dividing this mixture into at least two parts and cleaving the alkylaryl hydroperoxides in these parts in parallel at different temperatures.

The present invention further provides a mixture comprising phenol, acetone, AMS and cumene, obtainable by a process for the cleavage of alkylaryl hydroperoxides which comprises producing a mixture of a concentrate comprising at least one alkylaryl hydroperoxide to be cleaved and a cleavage product obtained from the cleavage of an alkylaryl hydroperoxide, dividing this mixture into at least two parts and cleaving the alkylaryl hydroperoxides in these parts in parallel at different temperatures.

The process of the invention has the advantage that, in contrast to conventional processes, the thermal post-treatment is integrated into the cleavage step. In this way, significantly less steam is required for heating the cleavage product during thermal post-treatment. If a sufficiently large quantity of heat of reaction is liberated in the cleavage at relatively high temperature, the use of steam for heating the cleavage product can be entirely eliminated. In contrast to processes or apparatuses in which steam or other suitable heat transfer media are used continually for heating the cleavage product, fouling occurs to a significantly lesser extent, if at all, when using the process of the invention for treating the cleavage product. In contrast to processes in which additional alkylaryl hydroperoxide is added to the cleavage product prior to a thermal after-treatment, the process of the invention requires no additional feed point with the safety devices known to those skilled in the art. The necessary apparatus is similarly simplified.

DETAILED DESCRIPTION OF THE INVENTION

The process of the invention is suitable for the acid-catalyzed cleavage of one or more alkylaryl hydroperoxides (AAHPs), including α-methylbenzyl hydroperoxide, α-methyl-p-methylbenzyl hydroperoxide, α,α-dimethylbenzyl hydroperoxide, also known as isopropylbenzene hydroperoxide or cumene hydroperoxide (CHP), α,α-methylethylbenzyl hydroperoxide, also known as sec-butylbenzene hydroperoxide, α,α-dimethyl-p-methylbenzyl hydroperoxide, α,α-dimethyl-p-ethylbenzyl hydroperoxide, α-methyl-α-phenylbenzyl hydroperoxide. The process of the present invention is particularly useful for the acid-catalyzed cleavage of mixtures of alkylaryl hydroperoxides comprising at least cumene hydroperoxide (CHP). The process of the invention is very particularly suitable for the cleavage of CHP.

The process of the invention is described below using the acid-catalyzed cleavage of CHP to give phenol and acetone as an example, without the process of the invention being restricted to this embodiment.

The process of the invention for the cleavage of alkylaryl hydroperoxides comprises producing a concentrate mixture comprising at least one alkylaryl hydroperoxide to be cleaved and a cleavage product obtained from the cleavage of at least one alkylaryl hydroperoxide, dividing this mixture into at least two parts and cleaving the alkylaryl hydroperoxides in these parts of the mixture in parallel at different temperatures.

The concentrate can be obtained, for example, as a mixture of the technical grade product of alkylaryl hydroperoxide generated by the oxidation of an alkenylaryl hydrocarbon. Such processes are well known in the art. In the case where CHP is the oxidation product other compounds including dicumyl peroxide (DCP) in small amounts may be present.

The cleavage product of an alkylaryl hydroperoxide may be obtained, for example, from the Hock process, or other similar processes in which an alkylaryl hydroperoxide is reacted with acid. In addition to a cleavage product such as phenol, the cleavage product may contain an aqueous and organic phase which may contain a number of compounds including acetone, cumene, water, α-methylstyrene (AMS), dimethyl phenyl carbinol (DMPC) and dicumyl peroxide.

The concentrate mixture is produced by mixing the organic phase components of the cleavage product with the alkylaryl hydroperoxide. The order of addition is not important and the alkylaryl hydroperoxide may be added to the cleavage product or the cleavage product may be added to the alkylarylperoxide. Further components such as water, acetone or cumene may also be mixed with the concentrate. The concentrate mixture can be prepared at a temperature from 30° C. to 45° C. with or without an inert atmosphere.

The two or more parts of the mixture are preferably treated in such a way that one part is treated at a temperature of from 45 to 99° C., preferably from 45 to 90° C., to cleave alkylaryl hydroperoxides and another part is heated to temperatures above 100° C. to cleave alkylaryl hydroperoxides. In the case of the part heated to temperatures above 100° C., cleavage of alkylaryl hydroperoxides with integrated thermal post-treatment takes place. In the following descriptions, the cleavage of the alkylaryl hydroperoxides at a temperature of from 45 to 99° C., preferably from 45 to 90° C., is referred to as low-temperature cleavage and the cleavage of the other part of the alkylaryl hydroperoxides at temperatures above 100° C. is referred to as high-temperature cleavage.

The treatment at a temperature above 100° C., i.e. the high-temperature cleavage, converts by-products formed in the cleavage of alkylaryl hydroperoxides, or in a preceding step of the overall process, e.g. the oxidation, into useful products. In the case of the preparation of phenol and acetone by the Hock process, dimethyl phenyl carbinol (DMPC), for example, is formed in the oxidation and dicumyl peroxide (DCP) is formed from DMPC and cumene hydroperoxide (CHP) during the cleavage step. The process of the invention has the purpose of reducing the proportion of dimethyl phenyl carbinol (DMPC) and dicumyl peroxide (DCP) in the cleavage product formed during the cleavage of CHP, since these compounds react further with other compounds or with themselves to form high-boiling, tar-like compounds in the subsequent work-up of the cleavage product which customarily includes a plurality of distillation steps to separate the components. These high-boiling compounds can interfere in the later process steps for the work-up of the cleavage product. Furthermore, the formation of high boilers significantly reduces the yield in the overall process of the Hock phenol synthesis.

When the process of the invention is applied to the cleavage of CHP, the DMPC present in the mixture to be cleaved is cleaved into α-methylstyrene (AMS) and water and the DCP, which is likewise present, is cleaved into phenol, AMS and acetone, by the treatment at a temperature above 100° C. The AMS formed in these reactions can, in the later work-up of the cleavage product, be separated from the latter and hydrogenated to cumene, which can be recycled as starting material to the overall process for phenol production. In this way, yield losses caused by formation of by-products are reduced.

As described above, at least one part separated from the mixture is treated at a temperature of from 45 to 99° C., preferably a temperature of from 45 to 90° C. and very particularly preferably a temperature of from 45 to 75° C., to cleave at least one alkylaryl hydroperoxide. This low-temperature cleavage can be carried out in one or more cleavage reactors which have sufficiently good heat removal. To control the temperature, it can be advantageous to use a shell-and-tube heat exchanger, for example, as the cleavage reactor. However, it is also possible to use any other reaction apparatus which is capable of removing the heat of reaction liberated in the low-temperature cleavage. The low-temperature cleavage is preferably carried out in at least two cleavage reactors, very particularly preferably in at least three cleavage reactors. The cleavage reactors can be connected in parallel or in series. The cleavage reactors are preferably connected in series and have at least one facility for removing heat energy.

If the treatment of the mixture at a temperature of from 45 to 99° C. is carried out using more than one cleavage reactor, it can be advantageous for at least two of the cleavage reactors to have a temperature difference of from 0 to 10° C., preferably from 2 to 7° C. The temperature in at least one of the cleavage reactors is preferably from 45 to 75° C. and the temperature in at least one further cleavage reactor is preferably set so that it is 1–10° C. higher, preferably 2–5° C. higher, than that in the first cleavage reactor, and, if a further cleavage reactor is present, the temperature in it is from 45 to 75° C.

It can be advantageous for part or all of the low-temperature cleavage product obtained from the low-temperature cleavage to be used for producing the mixture of cleavage product and concentrate comprising alkylaryl hydroperoxide. Preference is given to using all of the low-temperature cleavage product for producing the mixture.

As described above, at least one other part of the mixture is treated at a temperature above 100° C. This part is preferably treated at a temperature of above 115° C., particularly preferably above 130° C. and very particularly preferably above 150° C. In this high-temperature cleavage, the appropriate part of the mixture is preferably heated to a temperature above 100° C. in a cleavage reactor by means of an exothermic reaction occurring in this cleavage reactor. It is possible to use different exothermic reactions for heating this part of the mixture. It is preferred that at least one of the exothermic reactions occurring in the cleavage reactor is the cleavage of an alkylaryl hydroperoxide. If the concentrate used for producing the mixture is a concentrate obtained in the Hock phenol synthesis, at least one of the exothermic reactions is the cleavage of cumene hydroperoxide.

In the case of the cleavage of CHP, it has been found that a major part of the conversion of DMPC into AMS and water corresponds to the thermodynamic equilibrium established at temperatures above 100° C., even if the conversion of DCP is incomplete. Thus, only the residual DCP content after thermal treatment of the appropriate part of the mixture has to be checked to set optimum conditions for operation above 100° C. The residual DCP content in the part of the mixture which has been thermally treated according to the invention at a temperature above 100° C. is preferably from 0.001 to 1% by weight, more preferably from 0.01 to 0.1% by weight. Higher values lead to deterioration in the selectivity of the overall process, as a result of these DCP losses, which can also lead to higher contents of o-cresol in the pure phenol, while low values of less than 0.01% by weight can lead to excessively high formation of high-boiling by-products from AMS or DMPC during the treatment of the part of the mixture at a temperature above 100° C. The residual DCP content is usually determined by analysis. For the reasons mentioned, the part of the mixture to be treated thermally in the high-temperature cleavage is heated to a temperature above 100° C., preferably above 115° C., particularly preferably a temperature above 130° C. and very particularly preferably a temperature from 150° C. to 175° C.

For the high-temperature cleavage of the alkylaryl hydroperoxides, this part is transferred to a reactor, preferably a reactor having the characteristics of a tube reactor, and heated to above 100° C. According to the invention, this part is heated using the heat of reaction generated by at least one exothermic reaction in the relevant part of the mixture. According to the invention, one of the exothermic reactions is the acid-catalyzed cleavage of CHP. Since the heating of the mixture using the heat of reaction of at least one exothermic reaction occurs directly, indirect heat transfer by means of heat transfer media for heating the part of the mixture can be completely eliminated.

The cleavage of DCP via CHP and DMPC into phenol, acetone and AMS likewise liberates heat of reaction which corresponds to a defined increase in the temperature of the relevant part of the mixture. This temperature difference is usually, depending on the initial DCP content, from 10 to 20° C. Typical DCP concentrations are in the range from 2 to 8% by weight. However, the process of the invention is not restricted to the DCP concentrations indicated.

The quantity of heat liberated in these above-mentioned exothermic reactions has to be taken into account in the calculation of the initial CHP concentration necessary in the mixture which is to be heated to a temperature above 100° C.

To reach the desired temperatures of above 100° C., preferably above 115° C., particularly preferably above 130° C. and very particularly preferably above 150° C., the part to be treated thermally preferably has a cumene hydroperoxide concentration of from 2 to 25% by weight before thermal treatment. The part preferably has a CHP concentration of from 5 to 20% by weight, very particularly preferably from 10 to 15% by weight. The CHP concentration necessary in the part depends on the initial temperature of the part and on the initial DCP concentration. To calculate the necessary CHP concentration, it is possible to employ the rule of thumb that the cleavage of a 1% strength by weight CHP solution liberates approximately the amount of heat necessary to increase the temperature of the solution from 6.8 to 7.0° C. Thus, a 6% strength by weight CHP solution is heated by from 40.8 to 42° C. as a result of cleavage of all the CHP. The rule of thumb applies to the solutions usually used in the cleavage of CHP. These usually comprise at least cumene, phenol and acetone but only small amounts (of from 0 to 15% by weight) of water. Owing to the relatively high heat capacity of water, the cleavage of CHP in a solution or dispersion comprising 99% by weight of water and 1% by weight of CHP would increase the temperature of this solution by only about 3.5° C. For parts having a water content which is higher than usual, the heating factor has to be determined specifically. This determination can be carried out in a manner known to those skilled in the art by simple preliminary tests.

According to the above-described rule of thumb, a part having, for example, an initial temperature immediately after division of the mixture of 40° C. and a DCP content of 4% by weight requires a CHP concentration in the part of about 8.5% by weight to achieve a final or treatment temperature of 115° C. in the high-temperature cleavage. To achieve a final temperature of 175° C. in the high-temperature cleavage, the CHP content of the part of the mixture would have to be about 20% by weight.

The time taken for the part to be heated to a temperature up to 100° C. in the high-temperature cleavage is usually less than 30 seconds, starting from the time at which the mixture is divided. In the subsequent actual high-temperature cleavage, the temperature of the mixture in the residence reactor rises to a temperature above 100° C. The residence time of the cleavage product mixture in the residence reactor depends on the strength of the acid. Depending on the acid strength, the residence time is usually from 5 to 600 seconds.

In a particularly preferred embodiment of the process of the invention, the above-mentioned information or rules of thumb are used for controlling the cleavage of cumene hydroperoxide. It is possible to calculate the initial CHP concentration in the mixture prior to division of the mixture into two parts from the temperature profile in the high-temperature cleavage reactor, which is determined essentially by the exothermic reaction of cumene hydroperoxide cleavage and the quantity of heat liberated in this reaction. The use of the high-temperature cleavage reactor as a calorimeter makes it possible to obtain information on the composition of the mixture which can be utilized for controlling the cleavage, in particular the high-temperature cleavage.

However, it can also be advantageous to equip the reactor, which has the characteristics of a tube reactor and in which the high-temperature cleavage of alkylaryl hydroperoxides in the part at a temperature above 100° C. takes place, with a means of removing heat energy. In this way, it is also possible to limit the maximum temperature at which the high-temperature cleavage of the alkylaryl hydroperoxide takes place in the case where the product stream has a composition at which the sum of the quantities of heat liberated in the exothermic reactions is greater than that required for heating the part of the mixture. The preferred maximum temperature for the high-temperature cleavage of the alkylaryl hydroperoxides in this part of the mixture is, in the case of the cleavage of CHP, below 200° C. If this temperature is exceeded in the thermal cleavage, increased formation of by-products by thermal decomposition is observed, which is associated with a reduction in the yield of phenol and/or AMS in the cleavage.

After the high-temperature cleavage of the alkylaryl hydroperoxides in this part by treatment at a temperature above 100° C., the high-temperature cleavage product obtained can be cooled in a cooler. The high-temperature cleavage product is preferably brought to a final temperature of usually from 40 to 70° C. It can be advantageous for the high-temperature cleavage product obtained by treatment at a temperature above 100° C. to be neutralized by means of at least one base before its temperature is reduced. Bases which can be used are organic or inorganic bases. Preference is given to using sodium hydroxide (NaOH) and/or sodium phenoxide (NaOphenyl). The base can be added hot or cold, i.e. at a temperature corresponding to ambient temperature, to the high-temperature cleavage product. The base is preferably added cold to the high-temperature cleavage product. The addition can be carried out by mixing the base into the high-temperature cleavage product by means of suitable apparatuses, e.g. one or more static mixers. The addition of base before cooling the high-temperature cleavage product makes it possible to stop acid-catalyzed reactions immediately after addition of the base, as a result of which, in particular, undesirable acid-catalyzed secondary reactions which can occur during cooling and up to the neutralization which usually takes place after cooling can be stopped. The base can be added as an aqueous solution. It can be advantageous for the addition of the base in aqueous solution to introduce water into the high-temperature cleavage product from the part treated at a temperature above 100° C. in such an amount that the water content in this cleavage product is above or below the saturation concentration for water or the water content corresponds to the saturation concentration for water.

The high-temperature cleavage product obtained from the treatment at a temperature above 100° C. is passed to further treatment or work-up. This high-temperature cleavage product from the CHP cleavage is usually worked up by separating acetone and phenol from one another, and from other compounds present in the high-temperature cleavage product, by distillation. The work-up of these cleavage product streams is known to those skilled in the art.

It may be advantageous to introduce water into the part to be treated thermally at a temperature above 100° C. before it enters the reactor in which the high-temperature cleavage is to take place. Particular preference is given to adding water to the respective part of the mixture prior to the high-temperature cleavage in such an amount that the concentration of water in this part of the mixture is from 0.1 to 3.0% by weight, preferably from 0.5 to 2% by weight and very particularly preferably from 0.5 to 1.0% by weight.

The process of the invention makes it possible, in the cleavage of CHP having a concentration of from 65 to 90% by weight in the CHP concentrate, to obtain a high-temperature cleavage product having a residual dicumyl peroxide content of from 0.001 to 1% by weight, very particularly preferably from 0.01 to 0.1% by weight, from the fraction treated at a temperature above 100° C. As a result of the use of the process of the invention in the cleavage of CHP, the high-temperature cleavage product has a DMPC concentration of from 0.05 to 0.2% by weight. CHP is no longer detectable in this high-temperature cleavage product.

The mixture of a concentrate comprising at least one alkylaryl hydroperoxide to be cleaved and a cleavage product is preferably produced by mixing the concentrate with the cleavage product in a ratio of from 1:100 to 1:1, particularly preferably from 1:50 to 1:5.

The concentrate comprising at least one alkylaryl hydroperoxide (AAHP) used for producing the mixture preferably comprises from 40 to 95% by weight of at least one alkylaryl hydroperoxide, particularly preferably from 50 to 90% of an alkylaryl hydroperoxide, and in the case of CHP particularly preferably from 65 to 90% by weight of at least CHP. Further constituents of the concentrate in the case of CHP can be, inter alia, cumene, DMPC, DCP, acetophenone, AMS and/or water.

Mixing is preferably carried out in such a way that the concentrate comprising alkylaryl hydroperoxides is sufficiently well mixed with the cleavage product. This can be ensured in a manner known to those skilled in the art, e.g. by means of internals which make complete mixing possible, such as static mixers. It is also possible to meter the concentrate comprising alkylaryl hydroperoxides into the cleavage product on the suction side of the pump which pumps the cleavage product. In this way, too, complete mixing of the cleavage product with the introduced concentrate is ensured. Sufficient mixing of the concentrate with the cleavage product is necessary to avoid local overheating of the mixture.

The cleavage product to be mixed with the concentrate comprising alkylaryl hydroperoxides preferably has, prior to mixing with the concentrate, a concentration of alkylaryl hydroperoxides of from 0 to 20% by weight, preferably from 1 to 10% by weight.

It can be advantageous for the cleavage product which is mixed with the concentrate to comprise an equimolar or almost equimolar amount of the main product of the cleavage reaction, for example a ketone and an aromatic containing at least one OH group. In the case of the cleavage of CHP, the cleavage product used for producing the mixture preferably comprises an equimolar amount of acetone and phenol.

However, it can likewise be advantageous for the cleavage product with which the concentrate is mixed to produce the mixture, to have, in the case of the cleavage of CHP, a molar ratio of acetone to phenol of from 1.1:1 to 4:1, preferably from 1.2:1 to 1.5:1. This can be achieved, for example, by adding a fraction of acetone obtained from the high-temperature cleavage product by distillation, to the low-temperature cleavage product as diluent. Such recirculation of acetone is described for another process for the cleavage of AAHPs in a similar manner, e.g. in U.S. Pat. No. 5,254,751.

In a very particularly preferred embodiment of the process of the invention, the cleavage product which is obtained from the cleavage of an alkylaryl hydroperoxide and which is used for producing the mixture of cleavage product and concentrate, is the low-temperature cleavage product from the low-temperature cleavage of at least one part. The cleavage product used is preferably the low-temperature cleavage product of a part which has been treated at a temperature of from 45 to 90° C. Very particular preference is given to using all of the cleavage product from the low-temperature cleavage for mixing with the concentrate.

When all of the low-temperature cleavage product is used for mixing the mixture of cleavage product and concentrate, the process of the invention is operated so that the cleavage of the alkylaryl hydroperoxides is carried out in at least two steps:

a) acid-catalyzed low-temperature cleavage of alkylaryl hydroperoxides in one or more cleavage reactors, with the low-temperature cleavage product being mixed with a concentrate comprising at least one alkylaryl hydroperoxide to produce a mixture, and b) carrying out a high-temperature cleavage using a part of the mixture of the cleavage product from step a) and a concentrate comprising alkylaryl hydroperoxide, with the appropriate part of the mixture heated in a reactor and the heat of reaction of at least one exothermic reaction occurring in this reactor being utilized for heating this part of the mixture in the reactor.

In the process of the invention, the concentration of alkylaryl hydroperoxides in the parts are identical immediately before and thus also immediately after division of the mixture. When the process of the invention is used in the synthesis of phenol by the Hock method, the mixtures preferably comprise at least cumene hydroperoxide as alkylaryl hydroperoxide.

The parts of the mixture immediately after division of the mixture preferably comprise alkylaryl hydroperoxides, preferably at least cumene hydroperoxide, in a concentration of up to 25% by weight, particularly preferably from 5 to 20% by weight and very particularly preferably from 10 to 15% by weight.

The division of the mixture into at least two parts can be carried out during production of the mixture, after production of the mixture but before a first cleavage of at least one alkylaryl hydroperoxide in a reactor, or after production of the mixture and during, but at least before the completion of, at least one treatment of the mixture for the cleavage of at least one alkylaryl hydroperoxide in at least one reactor.

The division of the mixture is preferably carried out after the alkylaryl hydroperoxide to be cleaved has been mixed into the cleavage product and before this mixture enters a first cleavage reactor. In particular, it can be advantageous for the division of the mixture to be carried out immediately after the alkylaryl hydroperoxide to be cleaved has been mixed into the cleavage product.

Depending on the reactivity of the alkylaryl hydroperoxides added as concentrate, it can also be advantageous for the division of the mixture to be carried out after the alkylaryl hydroperoxide to be cleaved has been mixed into the cleavage product, after this mixture has entered at least one cleavage reactor, or after this cleavage mixture has left at least one cleavage reactor but at least before the mixture leaves a last cleavage reactor as cleavage product. Depending on the number of cleavage reactors used, the mixture can be divided at different points. Thus, when using three cleavage reactors connected in series, the mixture can be divided before it enters the first cleavage reactor, after it leaves the first cleavage reactor or after it leaves the second cleavage reactor. Taking off part of the mixture within the cleavage reactors is also possible and is within the scope of the process of the invention. In the following description, carrying out a first cleavage of alkylaryl hydroperoxides in at least one cleavage reactor before division of the mixture is referred to as precleavage.

If the division is carried out during, but at least before the completion of at least one treatment of the mixture for the cleavage of at least one alkylaryl hydroperoxide in at least one reactor, the process of the invention is said to be carried out with a precleavage step in which the mixture is treated in at least one cleavage reactor at from 45 to 99° C., preferably from 45 to 90° C. and very particularly preferably from 45 to 75° C., for the cleavage of at least one alkylaryl hydroperoxide. This precleavage is preferably carried out in at least one reactor which is equipped with a facility for the removal of heat energy, e.g. a heat exchanger.

Since a part of the mixture to be treated thermally is heated in a reactor for thermal treatment at above 100° C. and the heat of reaction of at least one exothermic reaction occurring in this reactor is used for heating the part of the mixture to be treated thermally in the reactor and preferably at least one of these exothermic reactions is the cleavage of an alkylaryl hydroperoxide, selection of the point at which the division of the mixture is to be carried out makes it possible to obtain a concentration of alkylaryl hydroperoxide in the parts of the mixture, in particular in the part of the mixture which is to be heated to a temperature above 100° C., which is just sufficient for the heat energy liberated in the exothermic reactions occurring in this reactor to be just sufficient to achieve the desired temperature in the reactor.

Depending on the concentration and amount of the concentrate comprising at least one alkylaryl hydroperoxide which is added to the cleavage product, and also the heat energy which is liberated in the exothermic reaction, the mixture is divided into at least two parts after a reaction time of from 0.01 to 600 seconds, preferably from 0.1 to 120 seconds, after production of the mixture of concentrate comprising alkylaryl hydroperoxide to be cleaved and cleavage product.

The ratio of the quantity of the part which is fed to the low-temperature cleavage to the quantity of the part which is fed to the high-temperature cleavage corresponds, when all of the low-temperature cleavage product is used for producing the mixture, to the mixing ratio of the quantity of cleavage product to the quantity of concentrate comprising alkylaryl hydroperoxide used for producing the mixture.

The process of the invention can be used for preparing phenol by cleavage of cumene hydroperoxide by producing a mixture of a concentrate comprising at least one alkylaryl hydroperoxide to be cleaved and a cleavage product obtained from the cleavage of an alkylaryl hydroperoxide, dividing this mixture into at least two parts and cleaving the alkylaryl hydroperoxides in these two parts in parallel at different temperatures.

The process of the invention makes it possible to obtain a mixture comprising phenol, acetone, AMS and cumene.

The process of the invention can, as indicated above, be employed in all processes in which alkylaryl hydroperoxides are cleaved. Alkylaryl hydroperoxides may be, for example, cumene hydroperoxide, sec-butylbenzene hydroperoxide, and also substituted alkylbenzene hydroperoxides or alkyl hydroperoxides of other aromatics such as naphthalene. The process of the invention is preferably used in cleavage of alkylaryl hydroperoxides in which the cleavage is an exothermic reaction. It is also possible to use the process of the invention for the cleavage of concentrates which comprise more than one alkylaryl hydroperoxide. In this case, at least one of the cleavage reactions has to be an exothermic reaction. The process of the invention is very particularly preferably used in the acid-catalyzed cleavage of CHP into phenol and acetone with combined thermal post-treatment of the cleavage product.

The process of the invention can be carried out continuously or batchwise. Preference is given to carrying out the process of the invention continuously.

The process of the invention can be carried out so that the acid-catalyzed cleavage of alkylaryl hydroperoxides occurs in a homogeneous phase or in a heterogeneous phase. If the low-temperature cleavage is carried out in a heterogeneous phase, it is necessary for a heterogeneous catalyst also to be present in the high-temperature cleavage. If the process is carried out so that a precleavage step takes place, a heterogeneous catalyst also has to be present in the precleavage step. Catalysts which can be used in a heterogeneous or homogeneous phase are all catalysts known in the art. The cleavages in the process of the invention, i.e. the precleavage, the low-temperature cleavage and the high-temperature cleavage, are preferably carried out in a homogeneous phase.

Sulfuric acid is preferably used as catalyst for the cleavage of alkylaryl hydroperoxide or of CHP. The mixture preferably has a sulfuric acid concentration of from 50 to 1000 ppm by weight. The catalyst is preferably added to the cleavage product used for producing the mixture.

It can be advantageous to alter the acid activity, i.e. the acid strength, of the part of the mixture which is fed to high-temperature cleavage. The acid strength is dependent on the acid concentration and the concentration of water in the cleavage mixture. The higher the water content of the cleavage mixture, the more acid has to be added to the mixture to achieve the same acid activity, with the acid strength being proportional to the square of the water concentration. Thus, for example, the acid strength of a cleavage mixture solution containing 200 ppm by weight of sulfuric acid and 2% by weight of water is only about one sixteenth of the acid strength of a cleavage mixture solution containing 200 ppm by weight of sulfuric acid and 0.5% by weight of water.

The ideal acid strength and thus the ideal composition of the mixture, or of the parts of the mixture, in terms of the acid concentration and water concentration can be determined by simple preliminary tests. In the case of mixtures having a water concentration of typically up to 2% by weight, a sulfuric acid concentration of from 100 to 500 ppm by weight in the mixture has been found to be particularly advantageous. To increase the acid strength, it is usual to add further sulfuric acid. To lower the acid strength, it is possible to add a base, e.g. sodium phenoxide, ammonia or sodium hydroxide, or water to the mixture. Preference is given to adding water to the mixture.

FIG. 1 schematically shows a process for the cleavage of CHP according to the prior art (DE 100 21 482). A concentrate comprising CHP to be cleaved is fed via a line (a) into a first reactor, the cleavage reactor. The cleavage reactor (R1) does not have to be only one reactor which can, for example, be configured as a tube reactor with recirculation or as a backmixed apparatus; it is also possible for the cleavage reactor to comprise a plurality of reactors connected in series. The cleavage product leaving the cleavage reactor is, in the case of a tube reactor, at least partly recirculated via a line (c) to the cleavage reactor. When using a homogeneous catalyst, this can be introduced into the cleavage product via line (s). Part of the cleavage product mixture is conveyed via line (b) into a second reactor (R2) in which the thermal post-treatment takes place. Upstream of the reactor (R2), cumene hydroperoxide (CHP) and optionally water ($H_2O$) can additionally be fed via two lines into the cleavage product mixture. The thermally-treated cleavage product mixture leaves the reactor (R2) via line (d) and can be passed to work-up.

Figure 2:
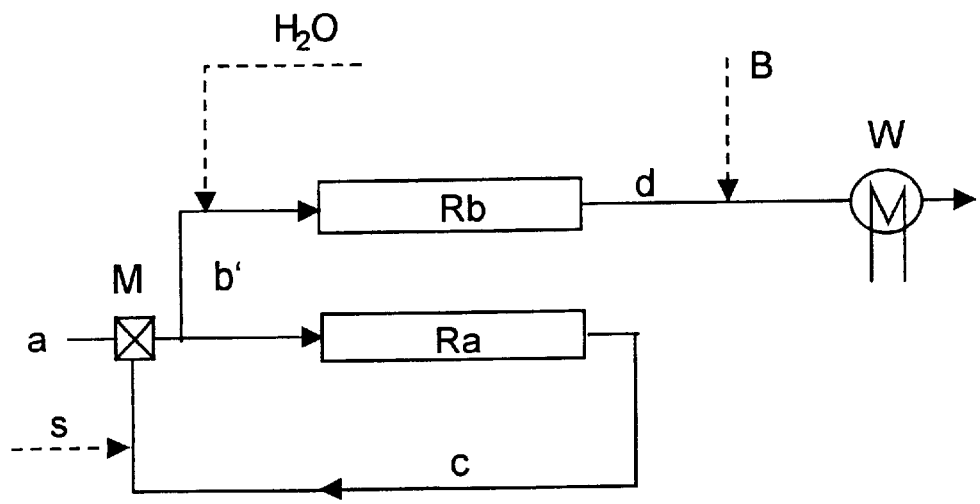

FIG. 2 schematically shows a process according to the invention for the cleavage of CHP. A concentrate comprising CHP to be cleaved is fed via line (a) into a mixer (M) where it is mixed with the cleavage product (c) from the reactor (Ra) to form a mixture. When using a homogeneous catalyst, it can be introduced via line (s) into the cleavage product (c). Part of the mixture from the mixer (M) is fed into a first reactor (Ra), the low-temperature cleavage reactor. The low-temperature cleavage reactor (Ra) can be not only a single reactor which can, for example be configured as a tube reactor with recirculation or as a backmixed apparatus, but the low-temperature cleavage reactor can also comprise a plurality of reactors connected in series. The low-temperature cleavage product leaving the low-temperature cleavage reactor is, in the case of a tube reactor, recirculated through line (e) via the mixer (M) to the low-temperature cleavage reactor. Part of the mixture is, before the mixture enters the reactor (Ra) branched off via line (b') and fed to a second cleavage reactor (Rb), the high-temperature cleavage reactor, in which the thermal high-temperature cleavage takes place. Upstream of the reactor (Rb), water ($H_2O$) can optionally be introduced via a line into this part of the mixture. The high-temperature cleavage product leaves the reactor (Rb) via line (d) and can be passed to work-up. Heat can be removed from the high-temperature cleavage product by means of the heat exchanger (W). A base (B) can optionally be added to the high-temperature cleavage product before it enters the heat exchanger.

Figure 3:
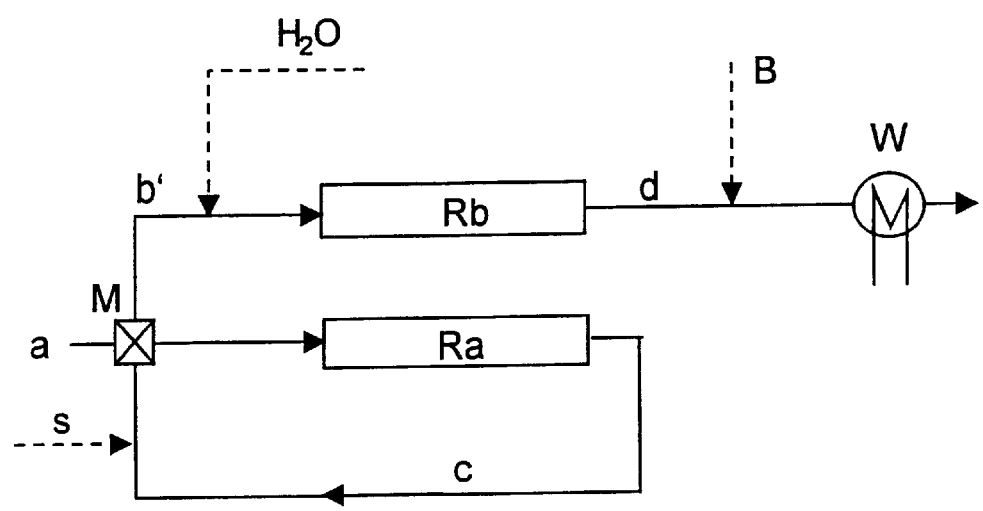

FIG. 3 schematically shows a further embodiment of the process of the invention for the cleavage of CHP. A concentrate comprising the CHP to be cleaved is fed via line (a) into a mixer (M) where it is mixed with the cleavage product (c) from the reactor (Ra) to form a mixture. When using a homogeneous catalyst, this can be introduced via line (s) into the cleavage product (c). Part of the mixture from the mixer (M) is fed into a first reactor (Ra), the low-temperature cleavage reactor. The low-temperature cleavage reactor (Ra) does not have to be only a single reactor which can be configured, for example, as a tube reactor with recirculation or as a backmixed apparatus; it is also possible for the low-temperature cleavage reactor to comprise a plurality of reactors connected in series. The low-temperature cleavage product leaving the low-temperature cleavage reactor is, in the case of a tube reactor, recirculated via line (c) to the mixer (M). Part of the mixture is conveyed from the mixer (M) via line (b') to a second cleavage reactor (Rb), the high-temperature cleavage reactor, in which the high-temperature cleavage takes place. Upstream of the reactor (Rb), water ($H_2O$) can optionally be introduced via a line into this part of the mixture. The thermally cleaved high-temperature cleavage product leaves the reactor (Rb) via line (d) and can be passed to work-up. Heat can be removed from the high-temperature cleavage product by means of the heat exchanger (W). A base (b) can optionally be added to the high-temperature cleavage product before it enters the heat exchanger.

Figure 4:
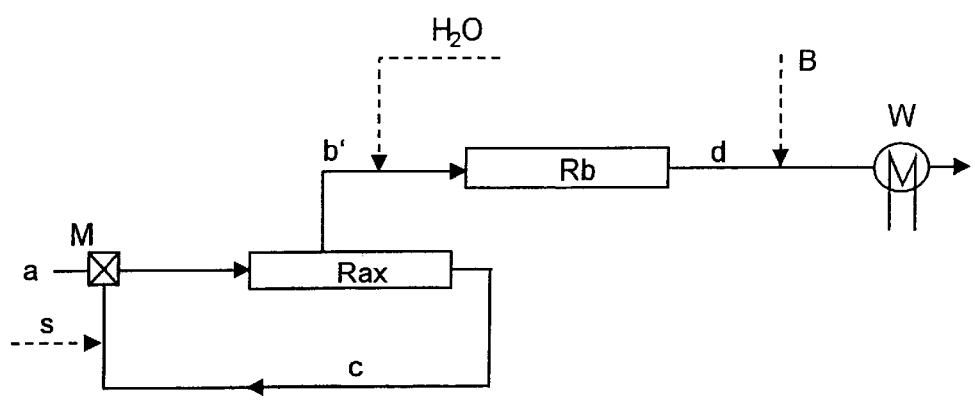

FIG. 4 schematically shows a further embodiment of the process of the invention for the cleavage of CHP. A concentrate comprising the CHP to be cleaved is fed via line (a) into a mixer (M) where it is admixed with the cleavage product c from the reactor (Rax) to form a mixture. When using a homogeneous catalyst, this can be introduced via line (s) into the cleavage product (c). Part of the mixture from the mixer (M) is fed into a first reactor (Rax), the low-temperature cleavage reactor, which is divided into a region in which precleavage takes place and a region in which the low-temperature cleavage is carried out. The low-temperature cleavage reactor (Rax) can be, for example, a tube reactor. The low-temperature cleavage product leaving the low-temperature cleavage reactor is, in the case of a tube reactor, recirculated via line (c) to the mixer (M). Part of the mixture from the precleavage step in the low-temperature cleavage reactor (Rax) is conveyed via line (b') to a second cleavage reactor (Rb), the high-temperature cleavage reactor, in which the high-temperature cleavage takes place. Upstream of the reactor (Rb), water ($H_2O$) can optionally be introduced via a line into the part of the mixture coming from the precleavage step. The thermally cleaved high-temperature cleavage product leaves the reactor (Rb) via line (d) and can be passed to work-up. Heat can be removed from the high-temperature cleavage product by means of the heat exchanger (W). A base (B) can optionally be added to the high-temperature cleavage product before it enters the heat exchanger.

Figure 5:
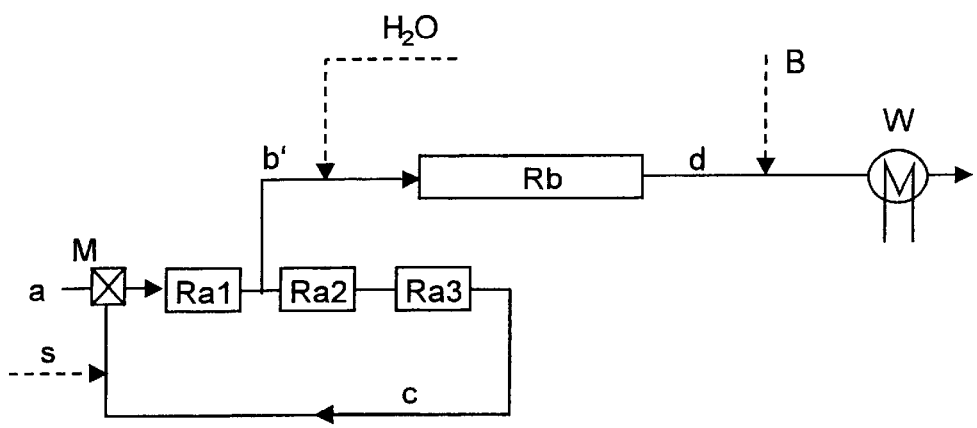

FIG. 5 schematically shows a further embodiment of the process of the invention for the cleavage of CHP. A concentrate comprising the CHP to be cleaved is fed via line (a) into a mixer (M) in which it is mixed with the cleavage product (c) from the reactor (Ra3) to form a mixture. When using a homogeneous catalyst, this can be introduced into the cleavage product (c) via line (s). The mixture from the mixer (M) is fed into a first precleavage reactor (Ra1). Part of the mixture leaving this reactor is transferred to a low-temperature cleavage reactor (Ra2) and the mixture leaving this is in turn transferred to a second low-temperature cleavage reactor (Ra3). The low-temperature cleavage product leaving the low-temperature cleavage reactor (Ra3) is recirculated via line (c) to the mixer (M). Part of the mixture from the precleavage step, which comes from the precleavage reactor (Ra1), is conveyed via line (b') to a high-temperature cleavage reactor (Rb) in which the high-temperature cleavage takes place. Upstream of the reactor (Rb), water ($H_2O$) can optionally be introduced via a line into this part of the mixture from the precleavage step. The high-temperature cleavage product leaves the high-temperature cleavage reactor (Rb) via line (d) and can be passed to work-up. Heat can be removed from the high-temperature cleavage product by means of the heat exchanger (W). A base (B) can optionally be added to the high-temperature cleavage product before it enters the heat exchanger.

German application 10051581.9 filed on Oct. 18, 2000 is hereby incorporated by reference.

All U.S. patents and all other documents referenced herein are incorporated herein by reference. Where a value range is stated, all values and sub-ranges therebetween are specifically included as if explicitly set forth.

EXAMPLE 1

According to the Prior Art 20 t/h of a concentrate having a CHP content of 68% by weight are fed into a cleavage process as shown in FIG. 1. The amount of recirculated cleavage product is 210 t/h, i.e. the recycled ratio is 10.5. The tube reactor is dimensioned so that at a sulfuric acid concentration of 320 ppm by weight, a water content of 0.7% by weight and a reaction temperature of 50° C., the CHP concentration at the outlet of the tube reactor is 0.5% by weight and the DCP concentration is 5.1% by weight. To be able to operate the subsequent thermal post-treatment at a temperature of, for example, 115° C., the CHP concentration of the cleavage product stream to the thermal post-treatment has to be increased from 0.5 to 6.4% by weight by addition of concentrate, i.e. 1.9 t/h of a 68% strength by weight concentrate have to be metered in.

EXAMPLE 2

According to the Invention

A cleavage process is carried out in a manner analogous to example 1, but part of the mixture of concentrate and cleavage product is taken off not at the outlet of the tube reactor but instead, as shown in FIG. 2, prior to entry into the low-temperature cleavage reactor installed as circulation reactor and fed to the high-temperature cleavage. Under the conditions described in example 1, the CHP concentration here is 6.4%, so that the same maximum temperature of about 115° C. is achieved in the high-temperature cleavage without additional CHP concentrate having to be added.

What is claimed is:

1. A process for acid-catalyzed cleavage of alkylaryl hydroperoxides, comprising producing a mixture of a concentrate wherein said mixture comprises at least one alkylaryl hydroperoxide to be cleaved and a cleavage product obtained from the cleavage of an alkylaryl hydroperoxide, dividing said mixture into at least two parts, and cleaving the alkylaryl hydroperoxides in said parts in parallel at different temperatures.

2. The process as claimed in claim 1, wherein the concentrations of alkylaryl hydroperoxides in the parts of the mixture immediately after division of the mixture are identical.

3. The process as claimed in claim 1, wherein at least one of the alkylaryl hydroperoxides is cumene hydroperoxide.

4. The process as claimed in claim 2, wherein the parts of the mixture immediately after division of the mixture comprise cumene hydroperoxide in a concentration of up to 20% by weight.

5. The process as claimed in claim 4, wherein the parts of the mixture immediately after division of the mixture each comprise cumene hydroperoxide in a concentration of from 10 to 15% by weight.

6. The process as claimed in claim 1, wherein the division of the mixture into at least two parts is carried out during production of the mixture.

7. The process as claimed in claim 1, wherein the division of the mixture into at least two parts is carried out after production of the mixture and before a first treatment of the mixture for the cleavage of at least one alkylaryl hydroperoxide in a reactor.

8. The process as claimed in claim 1, wherein the division of the mixture into at least two parts is carried out after production of the mixture and during and before completion of at least one treatment of the mixture for the cleavage of at least one alkylaryl hydroperoxide in at least one reactor.

9. The process as claimed in claim 8, wherein the mixture is treated in at least one reactor at from 45 to 75° C. for the cleavage of at least one alkylaryl hydroperoxide.

10. The process as claimed in claim 9, wherein the treatment is carried out in at least one reactor which is equipped with a facility for removing heat energy.

11. A process as claimed in claim 1, wherein the division of the mixture into at least two parts of the mixture is carried out from 0.01 to 600 seconds after production of the mixture.

12. The process as claimed in claim 1, wherein the mixture of a concentrate comprising at least one alkylaryl hydroperoxide to be cleaved and a cleavage product is produced by mixing the concentrate with the cleavage product in a ratio of from 1:100 to 1:1.

13. The process as claimed in claim 12, wherein the mixture of a concentrate comprising at least one alkylaryl hydroperoxide to be cleaved and a cleavage product is produced by mixing the concentrate with the cleavage product in a ratio of from 1:50 to 1:5.

14. The process as claimed in claim 1, wherein at least one of the parts of the mixture is treated at a temperature of from 45 to 90° C. for the cleavage of at least one alkylaryl hydroperoxide.

15. The process as claimed in claim 14, wherein the part of the mixture is treated at a temperature of from 45 to 75° C.

16. The process as claimed in claim 14, wherein the treatment is carried out in at least two cleavage reactors.

17. The process as claimed in claim 16, wherein the treatment is carried out in at least three cleavage reactors.

18. The process as claimed in claim 16, wherein the cleavage reactors are connected in series and have at least one facility for removing heat energy.

19. The process as claimed in claim 16, wherein the temperatures in at least two of the cleavage reactors have a temperature difference of from 0 to 10° C.

20. The process as claimed in claim 1, wherein at least one part of the mixture is treated at a temperature above 100° C.

21. The process as claimed in claim 1, wherein the part of the mixture is treated at a temperature above 130° C.

22. The process as claimed in claim 1, wherein the part of the mixture is heated to a temperature above 100° C. in a cleavage reactor by means of an exothermic reaction occurring in said cleavage reactor.

23. The process as claimed in claim 22, wherein one of the exothermic reactions occurring in the cleavage reactor is the cleavage of an alkylaryl hydroperoxide.

24. The process as claimed in claim 23, wherein the exothermic reaction is the cleavage of cumene hydroperoxide.

25. The process as claimed in claim 20, wherein water is added to the part of the mixture which is treated at a temperature above 100° C.

26. The process as claimed in claim 20, wherein, in the cleavage of cumene hydroperoxide, the residual dicumyl peroxide content of the cleavage product of the part of the mixture which was treated at a temperature above 100° C. is from 0.001 to 1% by weight.

27. The process as claimed in claim 26, wherein, in the cleavage of cumene hydroperoxide, the residual dicumyl peroxide content of the cleavage product of the part of the mixture which was treated at a temperature above 100° C. is from 0.01 to 0.1% by weight.

28. The process as claimed in claim 20, wherein the cleavage product of the part of the mixture which was treated at a temperature above 100° C. is cooled after the treatment.

29. The process as claimed in claim 28, wherein the cleavage product of the part of the mixture which was treated at a temperature above 100° C. is neutralized prior to cooling.

30. The process as claimed in claim 29, wherein the cleavage product of the part of the mixture which was treated at a temperature above 100° C. is neutralized with a base selected from the group consisting of aqueous solutions of NaOH, aqueous solutions of sodium phenoxide, organic solutions of NaOH, organic solutions of sodium phenoxide and mixtures thereof.

31. The process as claimed in claim 1, wherein the cleavage product which is obtained from the cleavage of an alkylaryl hydroperoxide and which is used for producing the mixture of cleavage product and concentrate is the cleavage product from the treatment of at least one of the parts of the mixture.

32. The process as claimed in claim 31, wherein the cleavage product is the cleavage product of a part of the mixture which has been treated at a temperature of from 45 to 90° C.

33. A process for preparing phenol by cleavage of cumene hydroperoxide, which comprises producing a mixture of a concentrate comprising at least one alkylaryl hydroperoxide to be cleaved and a cleavage product obtained from the cleavage of an alkylaryl hydroperoxide, dividing this mixture into at least two parts and cleaving the alkylaryl hydroperoxides in these parts in parallel at different temperatures.

* * * * *